(12) United States Patent
Shelton et al.

(10) Patent No.: US 8,105,341 B2
(45) Date of Patent: Jan. 31, 2012

(54) SUTURE REMOVAL DEVICE

(76) Inventors: Michelle Shelton, Detroit, MI (US);
Tyrone Secord, Rochester Hills, MI (US)

( * ) Notice: Subject to any disclaimer, the term of this patent is extended or adjusted under 35 U.S.C. 154(b) by 199 days.

(21) Appl. No.: 12/300,390

(22) PCT Filed: May 11, 2007

(86) PCT No.: PCT/US2007/068742
§ 371 (c)(1),
(2), (4) Date: Nov. 11, 2008

(87) PCT Pub. No.: WO2007/134214
PCT Pub. Date: Nov. 22, 2007

(65) Prior Publication Data
US 2009/0149868 A1    Jun. 11, 2009

Related U.S. Application Data

(60) Provisional application No. 60/799,747, filed on May 11, 2006.

(51) Int. Cl.
*A61B 17/32*     (2006.01)
(52) U.S. Cl. ............................. 606/138; 30/294; 30/314
(58) Field of Classification Search .................. 606/138; 30/289, 294, 314; 7/158, 121
See application file for complete search history.

(56) References Cited

U.S. PATENT DOCUMENTS

| 244,498 | A | * | 7/1881 | Terpany | 81/488 |
| D032,774 | S |   | 6/1900 | Maloney | |
| 716,454 | A |   | 12/1902 | Martin | |
| 768,083 | A |   | 8/1904 | Sickles et al. | |
| 1,498,753 | A | * | 6/1924 | Rendlich | 30/286 |
| 1,633,893 | A |   | 6/1927 | Hymer | |
| D097,456 | S |   | 11/1935 | Bernier | |
| 2,370,440 | A | * | 2/1945 | Beavin | 30/289 |
| 2,504,676 | A |   | 4/1950 | Franklin | |
| 2,547,376 | A |   | 4/1951 | Crawford | |
| 2,575,652 | A |   | 11/1951 | Bovee | |
| 2,610,399 | A | * | 9/1952 | Adams et al. | 30/286 |
| D169,572 | S | * | 5/1953 | Ament | D8/98 |
| D174,801 | S |   | 5/1955 | Davidson | |
| 2,764,814 | A | * | 10/1956 | Jecker | 30/294 |
| 2,900,722 | A |   | 8/1959 | Weisenburger | |
| 2,998,649 | A | * | 9/1961 | Miller et al. | 606/138 |
| 3,054,182 | A | * | 9/1962 | Whitton, Jr. | 606/138 |
| 3,266,493 | A | * | 8/1966 | Cummings | 606/138 |
| 3,624,683 | A | * | 11/1971 | Matles | 30/124 |
| 3,659,343 | A | * | 5/1972 | Straus | 30/124 |
| 3,754,290 | A | * | 8/1973 | Nicholson | 7/106 |

(Continued)

FOREIGN PATENT DOCUMENTS

JP     10257916     9/1998

(Continued)

*Primary Examiner* — Darwin Erezo
(74) *Attorney, Agent, or Firm* — Gifford, Krass, Sprinkle, Anderson & Citkowski, P.C.

(57) ABSTRACT

A hand-held suture removal device exhibiting a generally elongated body. First and second biasing portions extend from one end of the body and establish a gap therebetween. A blade extends from the body, typically from one of the biasing portions and in proximity to the gap defined between the biasing portions. The blade is manipulated to section a suture projecting from first and second locations of a patient's skin. A trailing edge of the suture is gripped between opposing and abutting surfaces established by the biasing portions and, upon deflecting of the device in a direction away from the patient, forcibly withdraws each of a plurality of sutures in rapid and successive fashion.

8 Claims, 3 Drawing Sheets

U.S. PATENT DOCUMENTS

| | | | | |
|---|---|---|---|---|
| 3,879,846 A | * | 4/1975 | Allen, Jr. | 606/138 |
| 3,972,117 A | * | 8/1976 | Fogg | 30/287 |
| 3,975,822 A | * | 8/1976 | Mabus | 30/294 |
| 4,026,295 A | * | 5/1977 | Lieberman | 606/167 |
| 4,034,473 A | * | 7/1977 | May | 606/138 |
| 4,053,979 A | * | 10/1977 | Tuthill et al. | 606/138 |
| 4,098,157 A | * | 7/1978 | Doyle | 606/138 |
| 4,384,406 A | * | 5/1983 | Tischlinger | 606/138 |
| 4,494,542 A | * | 1/1985 | Lee | 606/138 |
| 5,016,353 A | * | 5/1991 | Iten | 30/124 |
| 5,047,037 A | * | 9/1991 | Brandfield | 606/138 |
| 5,289,114 A | | 2/1994 | Nakamura et al. | |
| 5,331,739 A | | 7/1994 | Basangy | |
| 5,896,667 A | * | 4/1999 | Hawkins | 30/294 |
| 5,908,433 A | * | 6/1999 | Eager et al. | 606/170 |
| 5,970,615 A | | 10/1999 | Wall | |
| 6,820,624 B1 | | 11/2004 | Palmeri | |
| 7,674,267 B2 | * | 3/2010 | Lieberman | 606/79 |
| 7,958,583 B1 | * | 6/2011 | Heffner | 7/158 |
| 2002/0112352 A1 | | 8/2002 | Droin | |
| 2003/0075196 A1 | | 4/2003 | Fair | |

FOREIGN PATENT DOCUMENTS

| | | |
|---|---|---|
| JP | 2005206997 | 8/2005 |
| WO | WO-0013544 | 3/2000 |

* cited by examiner

US 8,105,341 B2

SUTURE REMOVAL DEVICE

REFERENCE TO RELATED APPLICATIONS

The present application claims the priority of U.S. Provisional Patent Application Ser. No. 60/799,747, filed May 11, 2006, the contents of which is incorporated herein by reference.

BACKGROUND OF THE INVENTION

The present invention is generally directed to a suture removal instrument. More specifically, the present invention teaches a hand-held suture removal device including a forward extending knife edge projecting from one of a pair of spaced apart and opposing biasing portions defined with the suture implement body, the same being squeezed together in manipulating fashion to forcibly withdraw from a patient's skin a medical suture sectioned by the knife edge.

SUMMARY OF THE INVENTION

The present invention is a hand-held suture removal device exhibiting a generally elongated shaped body having a specified shape and size and including first and second extending, opposing and spaced apart biasing portions establishing a gap therebetween. A blade extends forwardly from a selected biasing portion and exhibits an upper facing, typically arcuate extending, and incising knife edge located in proximity to the gap defined between the biasing portions, the blade being manipulated to section a suture projecting from first and second locations of a patient's skin. At that point, a selected trailing edge of the suture is gripped between opposing and abutting surfaces, these defining the biasing portions and, upon deflecting of the device in a direction away from the patient, forcibly withdraws each of a plurality of sutures in rapid and successive fashion.

Additional features include raised gripping surfaces associated with either or both of the opposing and inwardly deflectable abutting surfaces defined upon the biasing portions. The pluralities of linear extending and raised gripping surfaces are arrayed in offset and mating fashion between the opposing and inwardly deflectable biasing portion surfaces. The blade may further exhibit an outer extending and generally rounded/pointed lifting portion for raising a suture prior to sectioning thereof upon the knife edge.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1:
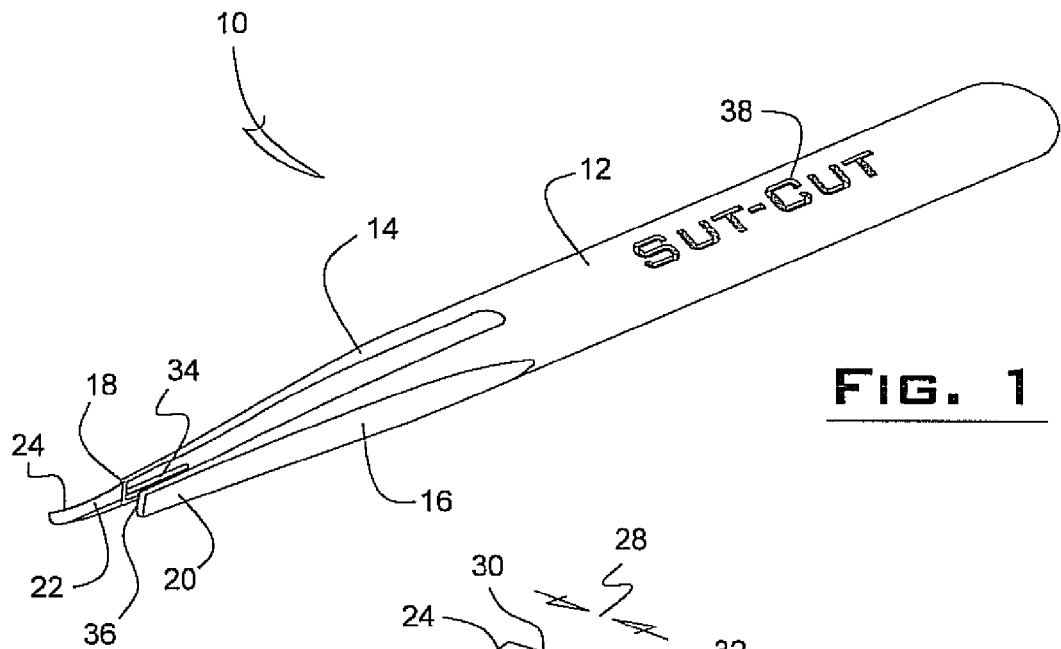
FIG. 1 is a perspective view of the suture removal device according to a preferred embodiment of the present invention.

Referring now to FIG. 1, a hand-held suture removal device is illustrated at 10 according to a preferred embodiment of the present invention. As previously stated, the present device teaches the sectioning and withdrawal of each of a plurality of sutures in rapid and successive fashion, and which is not possible through the use of such prior art tools as a suture knife and separate pair of tweezers.

Figure 3:
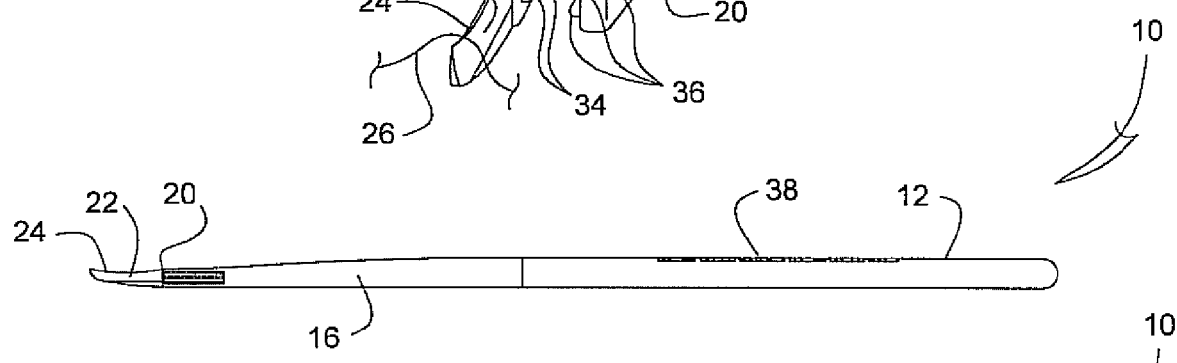
FIG. 3 is a side plan view of the suture removal device according to FIG. 1 of the present invention.
Figure 4:
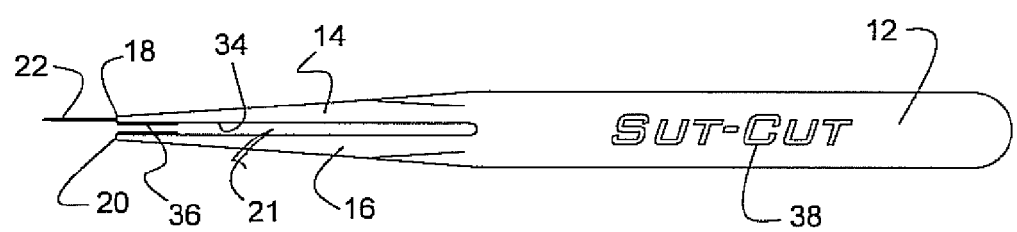
FIG. 4 is a top plan view of the present device and further illustrating the spacing established between the parallel extending and biasing/gripping portions associated with the suture implement body.

As viewed throughout the illustrations, the device includes a generally elongated shaped body, such as having a solid end portion 12, having a specified shape and size and including first and second extending and biasing portions 14 and 16 extending in substantially linear extending fashion and terminating at remote, narrowed and spatially arrayed ends 18 and 20, respectively. In this fashion, the biasing portions 14 and 16 establish a linear gap therebetween (see as best shown at 21 in FIG. 3).

A blade 22 extends in substantially linear fashion from a forward terminating edge of a selected one of the spaced apart and opposing biasing portions (in the illustrated instance the arrayed end 18 of biasing portion 14) in proximity to the gap defined between said biasing portions. The blade 22 further establishes a knife edge exhibiting a specified shape and size and having an arcuate upper extending and incising surface 24 terminating in a forward pointed end and which is particularly configured for sectioning a suture 26 extending from first and second locations of a patient's skin (see in particular enlarged partial view of FIG. 2).

In this fashion, the blade 22 is manipulated in a first motion to section the suture 26 projecting from the first and second locations of a patient's skin. At this point, a selected trailing edge of the previously cut suture (see as representatively further shown at 24' in FIG. 2) is gripped between the opposing and abutting surfaces defining the forward ends of the biasing portions 14 and 16 upon the same being biasingly deflected together in the direction of the arrows 28 and, upon deflecting of said device in a direction away from the patient, forcibly withdraws each of a plurality of sutures in rapid and successive fashion.

Figure 2:
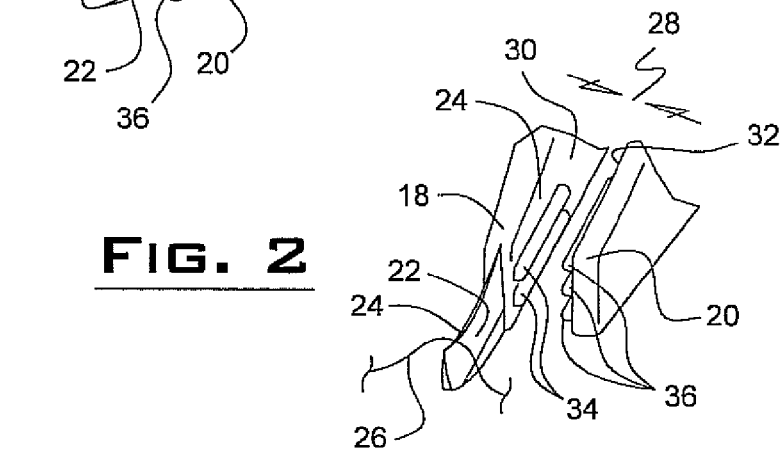
FIG. 2 is a partial enlarged end view of the present invention and further illustrating the features of the forward extending knife edge projecting from one of the pair of spaced apart and opposing biasing/gripping portions.

The suture removal device further exhibits at least one raised gripping surface associated with the opposing and inwardly deflectable abutting surfaces (further referenced at 30 and 32 in FIG. 2) and which are defined upon the inner opposing surfaces of the biasing portions 14 and 16. In particular, and as is best shown in FIG. 2, first 34 and second 36 pluralities of linear extending and raised gripping surfaces are arrayed in a combined linear extending and height offset and mating fashion between the opposing and inwardly deflectable biasing portion surfaces 30 and 32. In this fashion, the degree of frictional engaging (or gripping) is maximized in withdrawal of the sectioned and trailing edge of a previously sectioned suture.

Figure 5:
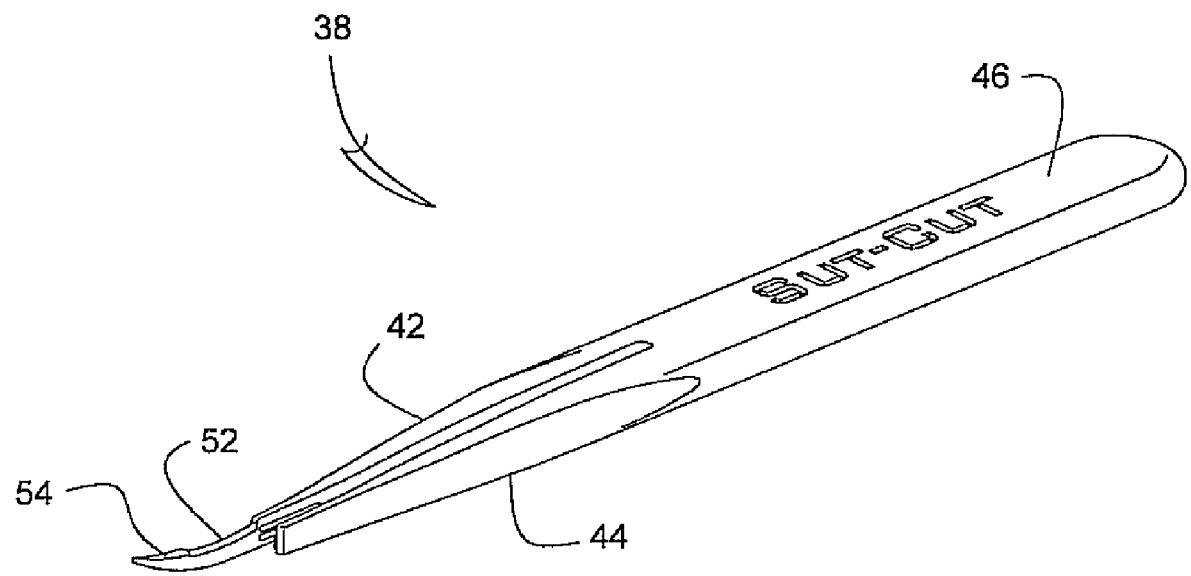
FIG. 5 is a perspective view of a suture removal device according to a yet further preferred embodiment and showing a variation in the blade configuration to mimic that associated with a seam ripper.

Referring now to FIG. 5, a perspective view is shown at 38 of a suture removal device according to a yet further preferred embodiment, and in particular illustrating a variation in an associated blade configuration 40, which mimics that associated with a conventionally known seam ripper. The device 38 is constructed similar to that previously illustrated in the variant of FIG. 1, and again includes first and second biasing portions 42 and 44 extending from a solid end portion 46.

Figure 6:
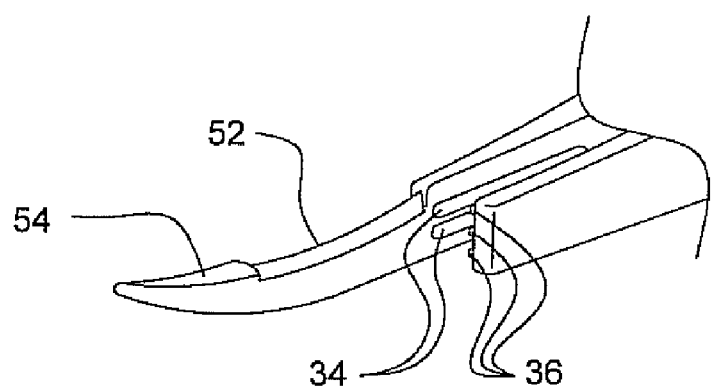
FIG. 6 is an enlarged sectional view of the blade configuration shown in FIG. 5.

As also shown in the enlarged sectional view of the blade configuration of FIG. 6, the blade 40 is insert molded into a selected plasticized (or alternatively metallic) body portion, e.g. portion 42. The blade also terminates in an arcuate defined inner end 48 and which, in combination with the curved upwardly facing profile of blade 40, mimics that of a seam ripper for effectively sectioning a suture for quick grasping and removal. As previously discussed, the blade can be constructed from such as a high grade stainless steel, as well as potentially a hygienic plastic.

Figure 7:
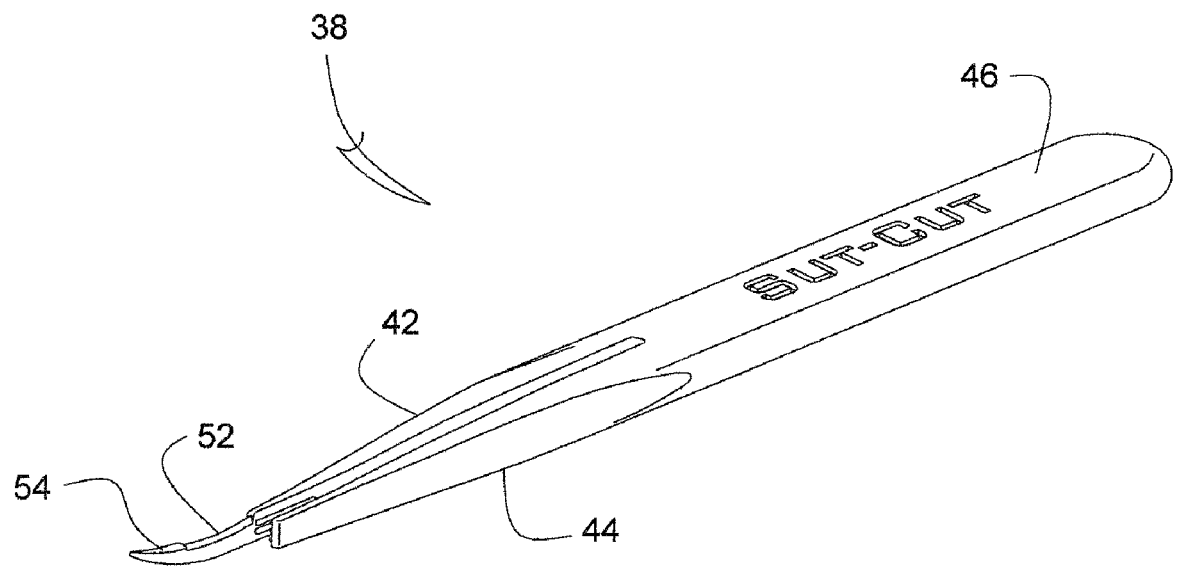
FIG. 7 is a perspective view of the suture removal device according to a still further preferred embodiment according to the present invention.
Figure 8:
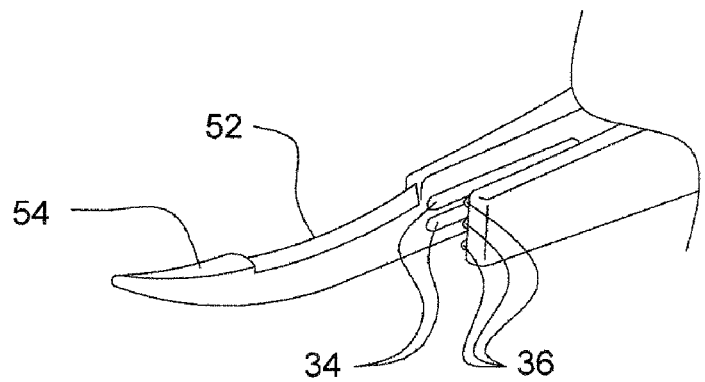
FIG. 8 is an enlarged sectional view of the blade configuration shown in FIG. 7.

Referring to FIG. 7, a still further perspective view is shown at 50 of the suture removal device according to a still further preferred embodiment and which teaches a substantially identical body design, with a further revised blade 52. The blade 52 in this variant is likewise arcuately (or curvedly) formed, and includes a recessed middle and upwardly facing cutting portion (see also enlarged sectional FIG. 8), and an outer most extending (slightly raised with rounded/pointed forward end) portion which functions to "lift" the suture and, thereby, to protect the skin, during sectioning thereof.

Additional features include the body having a specified shape and size and being constructed from at least one of a (sanitary) plastic, a stainless steel, and a chrome-plated steel material, each of which is intended to exhibit the necessary properties of deformability and durability associated with the effective manipulation of the biasing portions. The blade 18 may also be constructed of at least one of a plastic and a stainless steel material, provided it exhibits a satisfactorily configured and sharpened upper edge to effectively section the suture with a minimal degree of effort.

Other and additional features include the formation of a three-dimensional indicia imprint, see as best shown at 38, typically within the solid end portion 12 of said body. The manner of creating the indicia imprint is typically selected according to the type of molding, stamping or other mechanical process employed, this in turn usually dependent upon the type of material utilized in the formation of the suture removal device.

Having described my invention, other and additional preferred embodiments will become apparent to those skilled in the art to which it pertains and without deviating from the scope of the appended claims.

We claim:

1. A hand-held suture removal device, comprising:
a generally elongated shaped body having a specified shape and size and including first and second extending, inwardly deflectable and biasing portions establishing a linear gap therebetween, said body further comprising a solid gripping end portion extending at least a portion of an overall distance of said elongated body and from which extends said first and second biasing portions;
a blade extending from a forward terminating edge of a selected one of said biasing portions and forwardly of said other biasing portion, said blade further comprising a forward extending and upper facing knife edge facing away from the linear gap and terminating in a forward pointed end; and
said blade configured to be manipulated in a combined forward and upward motion to section a suture projecting from first and second locations of a patient's skin, wherein a selected trailing edge of the suture configured to be gripped between opposing and abutting surfaces defining said biasing portions upon said biasing portions being inwardly deflected to close the gap defined therebetween and such that said device is configured to be manipulated in a continuous motion following sectioning of the suture and away from the patient, forcibly withdrawing each of a plurality of sutures in rapid and successive fashion.

2. The device as described in claim 1, further comprising at least one raised gripping surface defined upon an opposing and inwardly deflectable surface of at least one of said biasing portions.

3. The device as described in claim 2, further comprising first and second pluralities of linear extending and raised gripping surfaces arrayed in offset and mating fashion between inwardly deflectable surfaces associated with said first and second biasing portions.

4. The device as described in claim 1, said body having a specified shape and size and being constructed from at least one of a plastic, a stainless steel, or a chrome-plated steel material.

5. The device as described in claim 4, said blade having a specified shape and size and being constructed of at least one of a plastic or a stainless steel material.

6. The device as described in claim 1, further comprising a three-dimensional indicia imprint formed within said solid end portion of said body.

7. The device as described in claim 1, said blade exhibiting a specified shape and size and exhibiting a "seam ripper" configuration with an arcuately defined inner end.

8. The device as described in claim 1, said blade exhibiting a specified shape and size and exhibiting an outer extending and generally rounded/pointed lifting portion for raising a suture prior to sectioning thereof upon said knife edge.

* * * * *